United States Patent
Gladkov

(10) Patent No.: US 8,758,710 B2
(45) Date of Patent: Jun. 24, 2014

(54) PROCESS FOR TREATING A FLUE GAS

(75) Inventor: Petr Gladkov, Toronto (CA)

(73) Assignee: E.T. Energy Corp., Mississauga, Ontario (CA)

( * ) Notice: Subject to any disclaimer, the term of this patent is extended or adjusted under 35 U.S.C. 154(b) by 554 days.

(21) Appl. No.: 13/160,719

(22) Filed: Jun. 15, 2011

(65) Prior Publication Data

US 2011/0305961 A1    Dec. 15, 2011

Related U.S. Application Data

(60) Provisional application No. 61/354,787, filed on Jun. 15, 2010.

(51) Int. Cl.
| B01D 53/34 | (2006.01) |
| B01D 53/50 | (2006.01) |
| B01D 53/56 | (2006.01) |
| B01D 53/62 | (2006.01) |

(52) U.S. Cl.
USPC ........ 423/210; 423/220; 423/230; 423/239.1; 423/244.07; 423/247

(58) Field of Classification Search
USPC .......... 423/210, 220, 230, 239.1, 244.07, 247
See application file for complete search history.

(56) References Cited

U.S. PATENT DOCUMENTS

| 3,837,820 A | 9/1974 | Kukin |
| 4,290,804 A | 9/1981 | Avery |
| 4,804,388 A | 2/1989 | Kukin |
| 4,842,617 A | 6/1989 | Kukin |
| 5,564,351 A | 10/1996 | Wagner |
| 6,932,321 B2 | 8/2005 | Baumann |
| 2003/0161773 A1 | 8/2003 | Liang et al. |
| 2004/0101460 A1 | 5/2004 | Arno et al. |
| 2007/0264184 A1 | 11/2007 | Krass |
| 2009/0071067 A1 | 3/2009 | MacPherson et al. |
| 2011/0305961 A1* | 12/2011 | Gladkov ........................ 429/417 |

FOREIGN PATENT DOCUMENTS

| CA | 634000 | 1/1962 |
| CA | 1289337 | 9/1991 |
| GB | 2242421 | 2/1991 |

OTHER PUBLICATIONS

Yuasa S. and Fukuchi A., "Ignition and combustion of magnesium in carbon dioxide streams", Symposium (International) on Combustion, vol. 25, Issue 1, 1994, pp. 1587-1594.

* cited by examiner

*Primary Examiner* — Timothy Vanoy
(74) *Attorney, Agent, or Firm* — Bereskin & Parr LLP/S.E.N.C.R.L., s.r.l.; Michael Fenwick

(57) ABSTRACT

A process for treating a flue gas is provided. The process comprises burning an amount of elemental magnesium in the flue gas, optionally to produce magnesium oxide and elemental carbon. A process for regenerating elemental magnesium from magnesium oxide is also provided, in addition to processes for producing energy from the elemental carbon.

32 Claims, 9 Drawing Sheets

PROCESS FOR TREATING A FLUE GAS

CROSS-REFERENCE TO RELATED APPLICATION

This application claims benefit under 35 U.S.C. §119(e) to U.S. provisional application Ser. No. 61/354,787, filed Jun. 15, 2010, incorporated herein by reference in its entirety.

FIELD

The disclosure relates to a process for treating a flue gas. Specifically, the disclosure relates burning elemental magnesium in a flue gas to treat the flue gas.

INTRODUCTION

The following is not an admission that anything discussed below is prior art or part of the common general knowledge of persons skilled in the art.

U.S. Pat. No. 3,837,820 (Kukin) discloses burning fuel in the presence of manganese and magnesium and adding additional amounts of magnesium to the products of combustion at relatively low temperatures to reduce undesirable emissions and improve internal boiler conditions.

U.S. Pat. No. 4,804,388 (Kukin) discloses providing a combination of manganese and magnesium to a combustion area, where the amounts of the two substances are within certain limits, to reduce noxious and undesirable emissions, improve internal boiler conditions, and employ lesser amounts of cold end additives.

U.S. Pat. No. 4,842,617 (Kukin) discloses adding a specific blend of coarse and fine particles of a magnesium compound to a relatively low temperature zone of a furnace system to reduce noxious and undesirable emissions and improve internal boiler conditions.

SUMMARY

The following summary is provided to introduce the reader to the more detailed discussion to follow. The summary is not intended to limit or define the claims.

According to one aspect, a process for treating a flue gas is provided. The process comprises burning an amount of elemental magnesium in the flue gas. In one embodiment, burning the amount of elemental magnesium in the flue gas provides for the removal of harmful or other undesirable chemicals from the flue gases, and improving electrical efficiency of the system.

The flue gas may comprise carbon dioxide, sulfur dioxide, carbon monoxide, and nitrogen dioxide. The flue gas may also comprise steam, oxygen and nitrogen. In one embodiment, the process of the disclosure treats oxide components including, but not limited to, sulfur dioxide, carbon monoxide, carbon dioxide or nitrogen dioxide.

In one embodiment, the flue gas is obtained from a power producing plant, such as a coal fired or natural gas fired thermoelectric power plant, a steel plant, a chemical plant, a cement plant, or any other industrial process or operation which produces a flue gas.

In some embodiments, during the burning step, at least a first portion of the amount of elemental magnesium may react with at least a portion of the carbon dioxide to yield magnesium oxide, carbon, and ultraviolet light. Further, during the burning step, at least a second portion of the amount of elemental magnesium may react with at least a portion of the carbon monoxide to yield magnesium oxide, carbon, and ultraviolet light. Further, during the burning step, at least a third portion of the amount of elemental magnesium may react with at least a portion of the sulfur dioxide to yield magnesium oxide, ultraviolet light, and at least one of elemental sulfur and magnesium sulfide.

At least a first portion of the nitrogen dioxide may be exposed to the ultraviolet light and may be decomposed into nitric oxide and monatomic oxygen. At least a second portion of the nitrogen dioxide may be exposed to the ultraviolet light and may be decomposed into monatomic nitrogen and monatomic oxygen. At least a portion of the nitric oxide may be exposed to the ultraviolet light and may be decomposed into monatomic nitrogen and monatomic oxygen. At least a first portion of the monatomic oxygen may react with a fourth portion of the amount of elemental magnesium to produce magnesium oxide. At least a first portion of the monatomic nitrogen may react with a fifth portion of the amount of elemental magnesium to produce magnesium nitride.

The process may further comprise igniting the amount of elemental magnesium.

The process may further comprise providing a solar cell and exposing the solar cell to at least a portion of the ultraviolet light to generate electricity from the solar cell.

The flue gas may further comprises water vapor, and at least a portion of the water vapor may react with at least a sixth portion of the amount of elemental magnesium to yield magnesium oxide and hydrogen gas.

The process may further comprise (i) passing the amount of elemental magnesium into a conduit, (ii) passing the flue gas into the conduit, and (iii) igniting and burning the amount of elemental magnesium in the conduit to yield a mixture of heated gases and powders.

The process may further comprise transporting the mixture to a heat transfer chamber wherein heat from the mixture is used to generate energy.

The process may further comprise separating the gases from the powders.

The amount of elemental magnesium may be in the form of a powder.

The flue gas may further comprise oxygen, and prior to step (iii), the process may further comprise pre-treating the flue gas to remove the oxygen. Pre-treating the flue gas may comprise exposing the flue gas to silane, whereby the silane reacts with the oxygen to yield silicon dioxide and water. Pre-treating the flue gas may further comprise exposing the flue gas to amorphous silicon, whereby the amorphous silicon reacts with monatomic nitrogen in the flue gas to yield silicon nitride.

The process may further comprise obtaining at least a magnesium oxide (MgO) fraction and a molecular carbon (C) fraction from the burning step. After the burning step, the magnesium oxide fraction may further be reacted with hydrogen iodide (HI) to obtain a magnesium iodide ($MgI_2$) fraction. The hydrogen iodide may further be obtained by contacting iodine ($I_2$) with water.

The process may further comprise heating the magnesium iodide fraction to a temperature suitable to obtain an elemental magnesium fraction and an iodine ($I_2$) fraction. The temperature suitable to obtain the elemental magnesium fraction is between about 600° C. and 800° C., optionally about 700° C.

The process may further comprise recycling the elemental magnesium fraction to the burning step. The iodine fraction may also be recycled and contacted with water to obtain the hydrogen iodide.

The process may further comprise utilizing the molecular carbon fraction in a direct carbon fuel cell to generate electrical energy and a carbon dioxide ($CO_2$) fraction. The carbon dioxide fraction may be treated in the burning step as defined above.

The process may further comprise obtaining the flue gas from natural gas, and the process further comprises obtaining at least a magnesium oxide (MgO) fraction, a molecular carbon (C) fraction and a hydrogen ($H_2$) gas fraction. The process may further comprise reacting the molecular carbon fraction with hydrogen gas in the presence of a suitable catalyst to obtain a methane gas fraction. The suitable catalyst may comprise powdered nickel.

The process may further comprise oxidizing the molecular carbon fraction to obtain a carbon dioxide fraction. In some embodiments, the carbon dioxide fraction and the hydrogen gas fraction are reacted in the presence of a suitable catalyst to obtain a methane gas fraction.

The process may further comprise burning the methane gas fraction to obtain thermal energy and a natural gas flue gas which is treated using the process as defined above.

The present disclosure also includes a closed loop energy production process in which a carbon-based fuel is burned to produce a flue gas containing at least a carbon dioxide fraction and/or a carbon monoxide fraction, the energy production process comprising:
   i) burning an amount of elemental magnesium in the flue gas to obtain a magnesium oxide (MgO) and a molecular carbon fraction;
   ii) reacting the magnesium oxide with hydrogen iodide (HI) to obtain a magnesium iodide ($MgI_2$) fraction;
   iii) heating the magnesium iodide to a temperature suitable to obtain an elemental magnesium fraction which is recycled to step (i), and
   iv)
      a. utilizing the molecular carbon in a direct carbon fuel cell and obtaining a second carbon dioxide fraction, and recycling the carbon dioxide fraction to step (i); or
      b. converting the molecular carbon fraction to a methane gas fraction which is burned to obtain the flue stream;
   wherein the thermal energy released from steps (i) and (iv) provide the energy for steps (ii) and (iii).

DRAWINGS

Reference is made in the detailed description to the accompanying drawings, in which.

DETAILED DESCRIPTION (I) Treatment of a Flue Gas

Various apparatuses or processes will be described below to provide an example of each claimed invention. No example described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. Applicant reserves the right to claim such apparatuses or processes in other applications.

The present disclosure relates to a process for treating a flue gas. As used herein, the term "flue gas" refers to an exhaust gas comprising harmful, undesirable or pollutant gases, including at least one of, and preferably all of, carbon dioxide ($CO_2$), carbon monoxide (CO), sulfur dioxide ($SO_2$), and nitrogen dioxide ($NO_2$). The flue gas may additionally include other gases such as oxygen ($O_2$), nitrogen ($N_2$), and water vapor ($H_2O$), as well as particulate matter. The flue gas may be an exhaust gas from, for example, a combustion process, a fireplace, an oven, a furnace, a boiler, a steam generator, car, a river craft and sea-crafts, or a power plant. Table 1 shows the composition of an exemplary flue gas, for example a flue gas from a coal burning plant.

TABLE 1

| Composition of Exemplary Flue Gas | |
| --- | --- |
| Compound | Vol. % of Flue Gas |
| $CO_2$ | 5-10 |
| CO | ≤0.1 |
| $O_2$ | 10-15 |
| $NO_x$ | 0.01-0.15 |
| $SO_2$ | ≤0.04 |
| $N_2$ and $H_2O$ | The balance |

Accordingly, in one embodiment, the process of the present disclosure is used to treat the flue gas from a coal-fired thermoelectric power plant.

The process for treating the flue gas comprises burning an amount of elemental magnesium (Mg) in the flue gas. By burning the elemental magnesium in the flue gas, the amount of harmful, undesirable, or pollutant gases in the flue gas, such as carbon dioxide ($CO_2$), carbon monoxide (CO), sulfur dioxide ($SO_2$), and nitrogen dioxide ($NO_2$), may be reduced. Particularly, as will be described in further detail below, by burning the elemental magnesium (Mg) in the flue gas, a series of chemical reactions take place to reduce the amount of harmful, undesirable, or pollutant gases in the flue gas.

Figure 1:
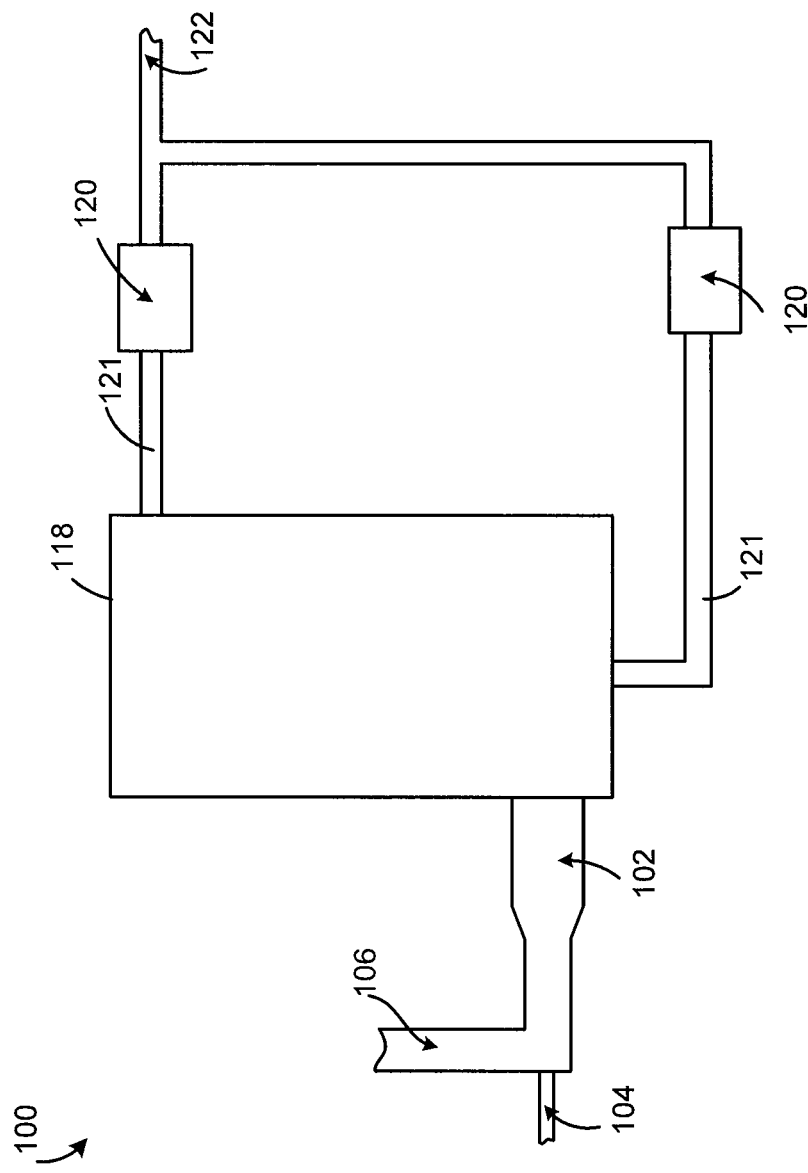
FIG. 1 is a schematic diagram of an example of a burning assembly.
Figure 2:
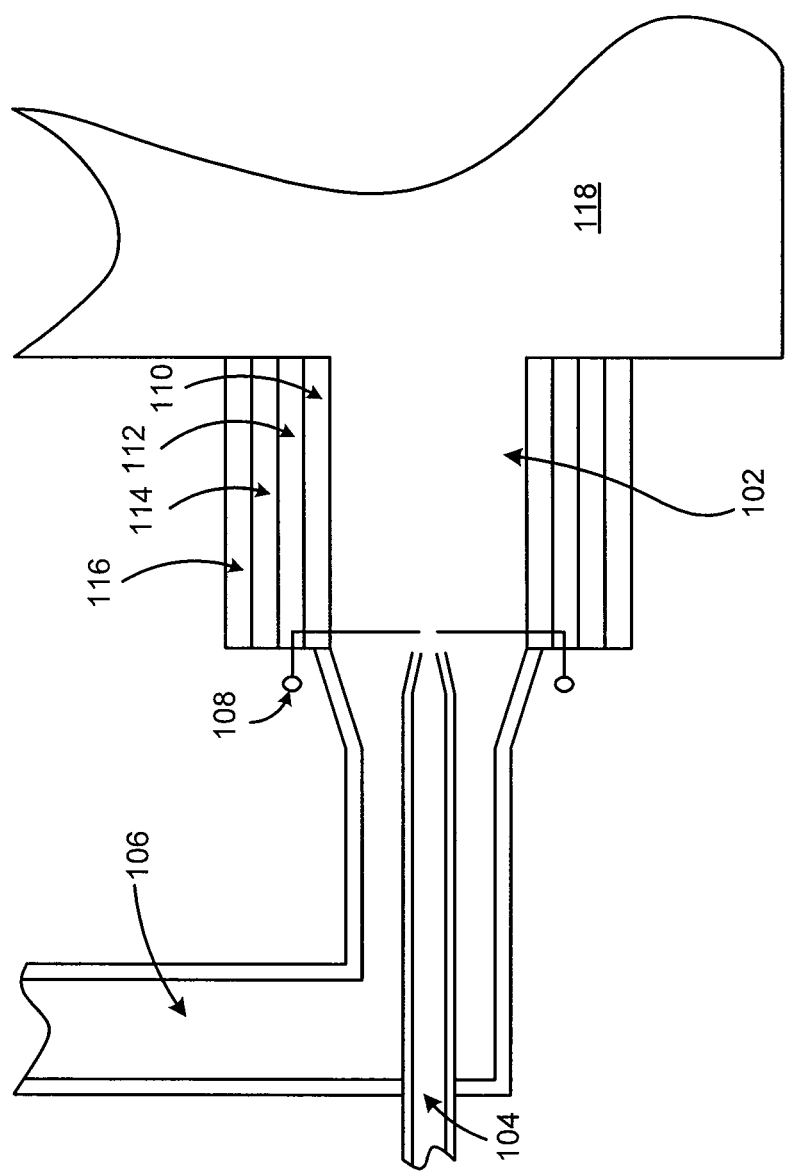
FIG. 2 is a cross-section taken through the burn conduit of FIG. 1.

Referring now to FIGS. 1 and 2, an exemplary burning assembly 100 for burning the amount of elemental magnesium in the flue gas is shown. The burning assembly 100 includes a burn conduit 102. The elemental magnesium may be passed into the burn conduit, via a magnesium inlet 104. The magnesium may be for example, in the form of a powder, a tape, rod, brick or any combination thereof. The flue gas may be passed into the conduit via a flue gas inlet 106. In one particular example, the flue gas may comprise amounts of each of carbon dioxide ($CO_2$), carbon monoxide (CO), sulfur dioxide ($SO_2$), and nitrogen dioxide ($NO_2$), as well as other gases such as oxygen ($O_2$), nitrogen ($N_2$), and water vapor ($H_2O$). The elemental magnesium and the flue gas may mix in the burn conduit 102, and the elemental magnesium may then be ignited in the conduit such that it burns in the flue gas as it passes through the burn conduit. Preferably, the flue gas and the elemental magnesium are continuously fed into the burn conduit 102 and continuously burned. However, in alternate examples, the magnesium may be burned in the flue gas in a batch process.

As mentioned above, by burning the elemental magnesium (Mg) in the flue gas, a series of chemical reactions take place to reduce the amount of harmful gases or undesirable in the flue gas. For example, at least a portion of each of the carbon dioxide ($CO_2$), carbon monoxide (CO), sulfur dioxide ($SO_2$) may react with at least a portion of the magnesium (Mg) to yield less harmful or less undesirable powders, as well as ultraviolet light (hv). At least a portion of the ultraviolet light (hv) may then catalyze the breakdown of at least a portion of the nitrogen dioxide ($NO_2$). Specifically, during burning of the magnesium in the flue gas, the following reactions may occur:

$$2Mg+CO_2 \rightarrow 2MgO+C+h\nu \quad (1)$$

$$Mg+CO \rightarrow MgO+C+h\nu \quad (2)$$

$$3Mg+SO_2 \rightarrow 2MgO+MgS+h\nu \quad (3)$$

$$2Mg+SO_2 \rightarrow 2MgO+S+h\nu \quad (4)$$

Reactions (1) to (4) may generate heat (Q), which together with the ultraviolet light (hv), may catalyze the breakdown of at least a portion of the nitrogen dioxide ($NO_2$), according to the following reactions:

$$NO_2+Q+h\nu \rightarrow NO+O \quad (5)$$

$$NO+Q+h\nu \rightarrow N+O \quad (6)$$

$$NO_2+Q+h\nu \rightarrow N+2O \quad (7)$$

At least a portion of the nitrogen (N) and oxygen (O) may then react with at least a portion of the amount of magnesium according to the following reactions:

$$Mg+O \rightarrow MgO \quad (8)$$

$$3Mg+2N \rightarrow Mg_3N_2 \quad (9)$$

Accordingly, at least a portion of the $CO_2$, $SO_2$, CO, and $NO_2$ is removed from the flue gas, and is converted to magnesium oxide (MgO), carbon (C), magnesium sulfide (MgS), sulfur (S), and magnesium nitride ($Mg_3N_2$), which may be less harmful, and may have commercial uses.

During the burning of the magnesium, additional side reactions may occur. For example, at least a portion elemental magnesium may burn with at least a portion of the water vapor to yield magnesium hydroxide powder ($Mg(OH)_2$), hydrogen gas ($H_2$), and ultraviolet light, according to the following reaction:

$$H_2O+Mg \rightarrow Mg(OH)_2+H_2+h\nu \quad (10)$$

Further, at least a portion of the elemental magnesium may burn with at least a portion of the oxygen in the flue gas to yield magnesium oxide powder, according to the following reaction:

$$2Mg+O_2 \rightarrow 2MgO+h\nu \quad (11)$$

The magnesium may be ignited in any suitable manner. For example, a plasma spark or electric arc apparatus 108 may be used to ignite the magnesium. The temperature required to ignite the magnesium may vary depending on the flow rate of the flue gas, the particular composition of the flue gas, the form of the magnesium, as well as other factors. For example, the ignition temperature of the flue gas may be between 650° C. and 730° C.

Continuing to refer to FIGS. 1 and 2, the burn conduit 102 may be of any suitable configuration. In some embodiments, the burn conduit 102 may be configured such that a portion of the ultraviolet light generated in reactions (1) to (4) is converted into electrical energy in the burn conduit 102. For example, referring to FIG. 2, in one embodiment, the burn conduit 102 may include a first layer 110 of quartz glass. A second layer 112, including a preferably cotton mesh tape impregnated with thorium nitrate $Th(NO_3)_4$ and ceric oxides $CeO_2$ may be positioned outwardly of the first layer 110, for example wrapped around the quartz glass. The heat generated by the burning of the magnesium may cause the cotton mesh to burn off, leaving behind a residue of thorium nitrate $Th(NO_3)_4$ and ceric oxides $CeO_2$. The residues, when exposed to the heat generated in reactions (1) to (4), emit visible light. A third layer 114 may be positioned outwardly of the second layer, and is preferably spaced from the second layer 112. The third layer 114 may comprise solar cells. The visible light given off by the thorium nitrate and ceric oxides may be converted to electrical energy by the solar cells. A fourth layer 116 may be positioned outwardly of the third layer 112, and may be any suitable layer for cooling the solar cells. In one embodiment, cooling the solar cells is provided for by an air-cooled system or a water-cooled system. In one embodiment, the fourth layer is a standard water-cooled (water jacket), wherein the space is filled with circulating water, as water does not absorb ultraviolet energy. In another embodiment, the fourth layer is an air-cooled jacket, wherein the space is filled with circulating air, as the ultraviolet rays converge to zero.

Referring back to FIG. 1, the burning assembly 100 may further include a chamber 118 provided downstream of the conduit 102. The burning of the magnesium in the conduit may yield a mixture of heated gases (including any remaining carbon dioxide, carbon monoxide, sulfur dioxide, nitrogen dioxide, oxygen, monatomic oxygen, nitric oxide, monatomic nitrogen, and water vapor, as well as nitrogen, and hydrogen), and powders (including magnesium oxide, carbon, magnesium sulfide, sulfur, magnesium nitride, magnesium hydroxide, and some remaining magnesium). The chamber 118 provides a volume for the heated gases to expand into out of the burn conduit 102, and provides a volume in which the powders may sediment. Further, the chamber 118 may be a heat transfer chamber. For example, the chamber 118 may be fitted with a water jacket, and heat from the gases and powders may be transferred to the water to generate steam, as is known in the art. The steam may be used, for example, in a steam turbine (not shown).

Continuing to refer to FIG. 1, from the heat transfer chamber 118, the mixture of gases and powders may travel to one or more separators 120 via chamber outlets 121, to separate the powders from the gases. The separators may include, for example, a cyclone, or a filter. The separated powders may be collected, and may optionally be further separated from each other. The powders may then be sold, or put towards any other suitable uses. The gases may then pass into an outlet conduit 122. From the outlet conduit 122, the gases, which may still heated, may be passed through one or more boilers or gas turbines (not shown), to generate energy. The gases may then be released to the atmosphere.

As mentioned above, during the burning of the magnesium, a side reaction may occur wherein a portion of magnesium burns with the oxygen in the flue gas. This reaction may be undesirable, as there may be no need to remove the oxygen from the flue gas, and as the reaction consumes magnesium. Accordingly, in some embodiments, the process may comprise a pre-treatment step, wherein prior to burning the magnesium in the flue gas, the flue gas is pre-treated to remove the oxygen. The pretreatment step may include exposing the flue gas to silane gas ($SiH_4$), so that the silane reacts with the oxygen to produce silicon dioxide ($SiO_2$) and water vapor ($H_2O$) according to the following reaction:

$$SiH_4 + 2O_2 \rightarrow SiO_2 + 2H_2O \quad (12)$$

Additionally, a side reaction may occur wherein some of the carbon dioxide in the flue gas reacts with the silane, according to the following reaction:

$$SiH_4 + 4CO_2 \rightarrow SiO_2 + 2H_2O + 4CO \quad (13)$$

In addition, monatomic nitrogen may be present in the flue gas. For example, the heat of reaction (12) may break down diatomic nitrogen in the flue gas into monatomic nitrogen. The pretreatment step may further include exposing the flue gas to amorphous silicon, so that the silicon reacts with monatomic nitrogen to yield silicon nitride according to the following reaction:

$$3Si + 4N \rightarrow Si_3N_4 \quad (14)$$

The silicon nitride may optionally be collected, and may be, for example sold. Further, reaction (14) may generate heat, which may be used to generate energy, as described below.

Figure 3:
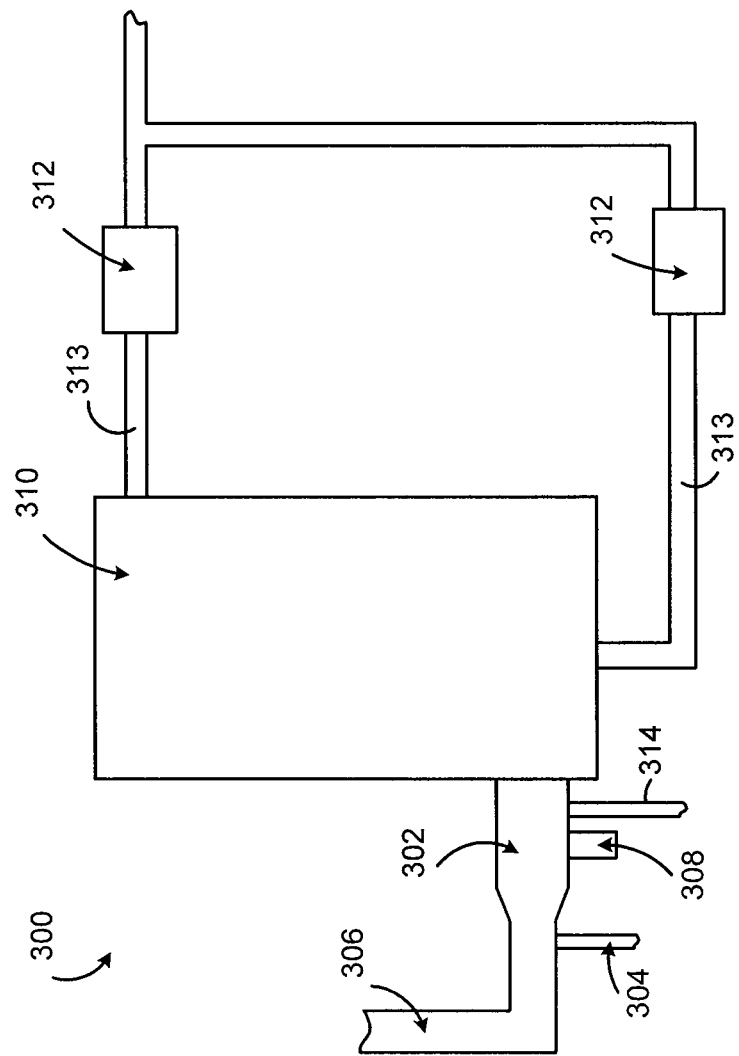
FIG. 3 is a schematic diagram of an example of a pre-treatment assembly.
Figure 4:
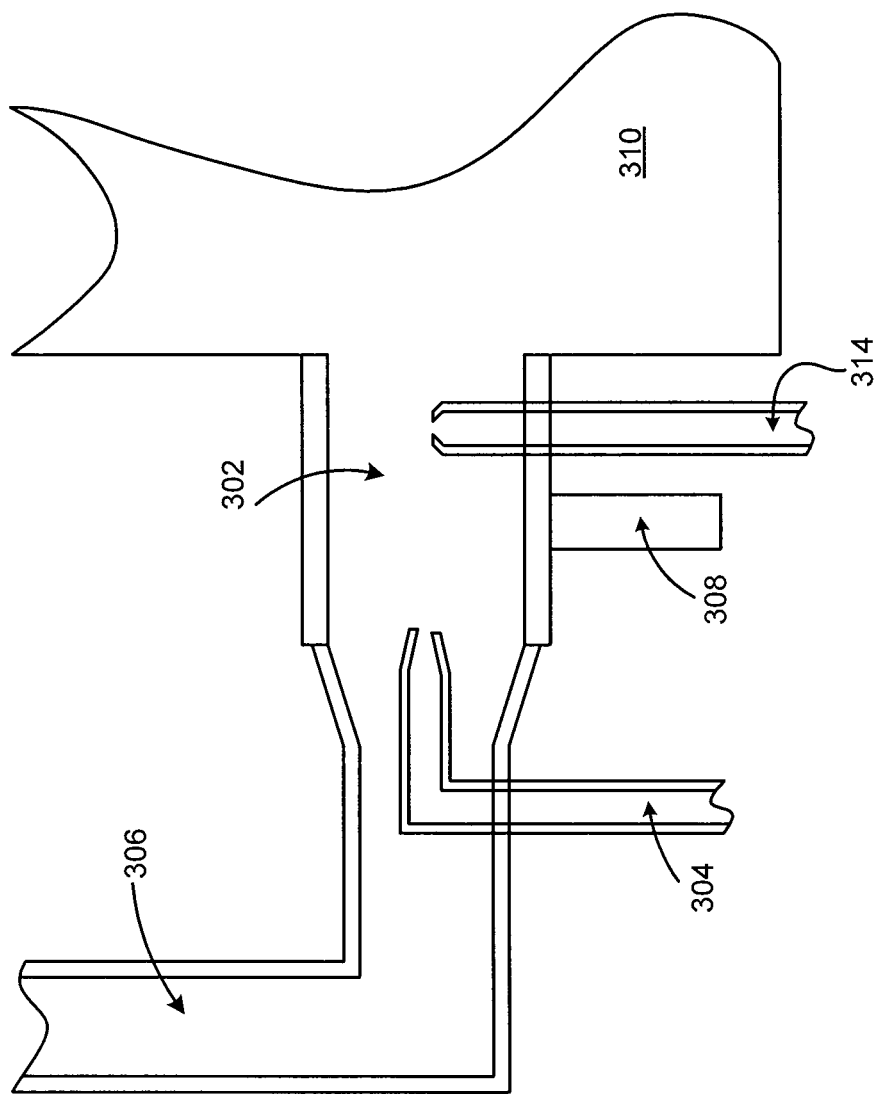
FIG. 4 is a cross-section taken through the pre-treatment conduit of FIG. 3.

Referring to FIGS. 3 and 4, an exemplary pre-treatment assembly 300 for carrying out the pre-treatment step is shown. The pre-treatment assembly 300 includes a pre-treatment conduit 302. The silane gas may be passed into the pre-treatment conduit via a silane inlet conduit 304. The flue gas may be passed into the pre-treatment conduit via a flue gas inlet conduit 306. The silane gas and the flue gas may mix in the pre-treatment conduit 302. In order for reaction (12) to occur, elevated temperatures may be required. For example, reaction (12) may require temperatures of up to 400° C. Accordingly, the pre-treatment conduit 302 may be heated, for example using a burner 308. As the silane gas and flue gases mix and pass through the heated conduit, reaction (12) may occur, and the amount of oxygen in the flue gas may be reduced. Additionally, reaction (13) may occur simultaneously with reaction (12).

Continuing to refer to FIGS. 3 and 4, the pre-treatment assembly further includes a silicon inlet 314, through which the amorphous silicon is introduced into the pre-treatment conduit 302. The amorphous silicon and the flue gas may mix in the pre-treatment conduit 302 downstream of the burner 308, and reaction (14) may occur.

Continuing to refer to FIGS. 3 and 4, the pre-treatment assembly 300 may optionally include a chamber 310 downstream of the pre-treatment conduit 302. The mixture exiting the pre-treatment conduit 302 may include heated gases (including carbon dioxide, carbon monoxide, sulfur dioxide, nitrogen dioxide, nitrogen, water vapor, any remaining silane, and a reduced amount of oxygen), and powders (including silicon dioxide and silicon nitride). The mixture may be passed from the pre-treatment conduit 302 into the chamber 310. The chamber 310 provides a volume for the heated gases to expand, and provides a volume for the powders to sediment. Further, chamber 310 may be a heat transfer chamber. For example, the chamber 310 may be fitted with a water jacket, and heat from the gases and powders may be transferred to the water to generate steam, as is known in the art. The steam may be used, for example, in a steam turbine.

Continuing to refer to FIGS. 3 and 4, from the chamber 310, the mixture of gases and powders may travel to one or more separators 312 via chamber outlets 313, to separate the powders from the gases. The separators may comprise, for example, a cyclone, or a filter. The powders may be collected. The gases, which have a reduced content of oxygen $O_2$, may then be forwarded to the burn conduit 102, via the flue gas inlet conduit 106.

In another embodiment of the disclosure, the process for treating a flue gas is used to treat the flue gas from a natural gas fired thermoelectric power plant.

The combustion of natural gas, primarily comprising methane ($CH_4$), generally proceeds according to reaction (15), while overall, the reaction proceeds according to reaction (16):

$$CH_4 + 2O_2 + 7.5N_2 \rightarrow CO_2 + 2H_2O + 7.5N_2 + heat \quad (15)$$

$$CH_4 + 2O_2 \rightarrow CO_2 + 2H_2O + heat \quad (16)$$

Natural gas is primarily composed of methane (about 83%-93%), with other components including ethane (2.4%-8.48%), propane (2.0%-4.4%) and butane (0.20%-5.44%), with other heavier components comprising less than about 1.5%.

As shown in reactions (15) and (16), the combustion of natural gas generates $CO_2$, while molecular carbon and carbon monoxide are also formed. In addition, these reactions may generate hydrogen gas ($H_2$) in addition to and/or instead of water ($H_2O$). Moreover, nitrogen oxides ($NO_x$) may form from diatomic nitrogen in the heat of the reaction.

Accordingly, when the flue gases generated from the combustion of natural gas are treated using the process of the present disclosure, the following reactions occur:

$$CO_2(g) + Mg(s) \rightarrow 2MgO(s) + C(s) \quad (17)$$

$$2H_2O(g) + Mg(s) \rightarrow Mg(OH)_2 + H_2(g) \quad (18)$$

$$Mg(OH)_2 \rightarrow (T \geq 450° C.) \rightarrow MgO(s) + H_2O(g) \quad (19)$$

$$2H_2O(g) + 2Mg(s) \rightarrow 2MgO(s) + 2H_2(g) \quad (20)$$

Accordingly, the main products generated by burning the flue stream from natural gas combustion are carbon, hydrogen gas and magnesium oxide.

(II) Regeneration of Elemental Magnesium

In another embodiment of the disclosure, there is also included a process for the regeneration of the elemental magnesium (Mg) used to treat the flue gas. As described above, burning elemental magnesium (Mg) in a flue gas results in the generation of magnesium oxide (MgO), in addition to other products (identified in reactions 1-4 above). Accordingly, in one embodiment, there is included a process for the regeneration of elemental magnesium from magnesium oxide, as detailed in the general reaction (21) below (other products such as C, MgS, etc. are not shown). In one embodiment, the regenerated elemental magnesium is recycled and used to treat additional flue gas.

$$Mg + flue\ gas \rightarrow MgO + heat \rightarrow \rightarrow Mg \quad (21)$$

In one embodiment of the disclosure, the magnesium oxide is converted to magnesium iodide ($MgI_2$), which is then heated to regenerate elemental magnesium as shown in general reaction (22). As heat energy is a basic by-product of thermoelectric power plants, the regeneration and recycling of elemental magnesium to be used for further treatment of flue gases does not require the use of additional electrical input. Accordingly, in one embodiment, the process to regenerate and recycle the elemental magnesium is a closed continuous process, in which the heat energy from the thermoelectric power plant, and also the heat from burning the elemental magnesium in the flue gas, is utilized to regenerate the elemental magnesium.

$$MgO \rightarrow MgI_2 + heat \rightarrow Mg \qquad (22)$$

In one embodiment, the magnesium iodide ($MgI_2$) is prepared from the magnesium oxide by contacting the MgO with hydrogen iodide (HI) as set out in reaction (23).

$$MgO + 2HI \rightarrow MgI_2 + H_2O \qquad (23)$$

The generation of hydrogen iodide is prepared as is known in the art by mixing iodine ($I_2$) in water, which forms hydrogen iodide, as set out in reaction (24), which forms an azeotropic mixture with water, containing about 57% HI with a boiling point of 127° C. In addition to the generation of hydrogen iodide, the unstable hypoiodous acid (HIO) is also formed, which decomposes to iodic acid ($HIO_3$) and iodine as shown in reaction (25). The iodine ($I_2$) generated from the decomposition of HIO, begins the process over again generating more HI, and accordingly, the process for the production of HI is continuous. The reaction generates about 57% HI, about 15.7% $HIO_3$, about 20% $H_2O$ and about 6.5% $I_2$.

$$2I_2 + 2H_2O \rightarrow 2HI + 2HIO \qquad (24)$$

$$5HIO \rightarrow HIO_3 + 2I_2 + 2H_2O \qquad (25)$$

Overall, the reaction of iodine and water proceeds as per the reaction (26).

$$5I_2 + 5H_2O \rightarrow 7HI + (7/5)HIO_3 + (4/5)H_2O + (4/5)I_2 \qquad (26)$$

In one embodiment, the hydrogen iodide reacts with magnesium oxide to form a mixture comprising magnesium iodide as shown in reaction (27).

$$2HI + MgO \rightarrow MgI_2 + H_2O \qquad (27)$$

In addition, the iodic acid formed in reaction (26) also reacts with magnesium oxide as shown in reaction (28), and the magnesium oxide also reacts with water to form magnesium hydroxide $Mg(OH)_2$ as shown in reaction (29).

$$2(HIO_3) + MgO \rightarrow Mg(IO_3)_2 + H_2O \qquad (28)$$

$$MgO + H_2O \rightarrow Mg(OH)_2 \qquad (29)$$

The magnesium hydroxide produced in reaction (29) reacts with the iodine ($I_2$) generated in reaction (28) to form magnesium iodide and magnesium iodate $Mg(IO_3)_2$ as shown in reaction (30). However, magnesium hydroxide will be continuously produced as the magnesium oxide is generated from burning in the flue gas.

$$6[Mg(OH)_2 + I_2] \rightarrow 5MgI_2 + Mg(IO_3)_2 + 6H_2O \qquad (30)$$

Magnesium iodide $MgI_2$ and $Mg(IO_3)_2$ are stable compounds which are readily soluble in water and are in the form of hydrates (such as magnesium iodide hexahydrate and octahydrate and magnesium iodate tetra-iodate and decahydrate).

Accordingly, after treatment with hydrogen iodide (HI), there will be present in the mixture magnesium iodide, magnesium iodate and magnesium hydroxide. In one embodiment, the excess magnesium hydroxide is removed by heating the mixture above at least 350° C., optionally 400° C., suitable above about 450° C. which converts the magnesium hydroxide to magnesium oxide, as shown in reaction (31), which can then be reacted through reaction (23).

$$Mg(OH)_2 + heat \rightarrow MgO + H_2O \qquad (31)$$

In another embodiment, the magnesium iodate is also removed by heating the mixture to above at least 600° C., optionally 650° C., suitably above at least 660° C., which converts the magnesium iodate to magnesium oxide and iodine ($I_2$) as shown in reaction (32).

$$Mg(IO_3)_2 + heat \rightarrow 5MgO + 5I_2 + (25/2)O_2 \qquad (32)$$

The iodine generated in reaction (32) sublimates and is recycled to reaction (18). In one embodiment, magnesium oxide (generated in reactions (31) and (32)) and magnesium iodide (generated in reaction (27)), are separated using any method which is able separate mixtures on the basis of weight and/or density differences of the components of the mixture, such as centrifugal separation, using a centrifuge. The separated magnesium oxide is returned to the reaction (27).

In another embodiment, the magnesium iodide is heated to a temperature of at least about 650° C., optionally about 675° C., suitably at least about 700° C., and decomposes as per the reaction (33).

$$MgI_2 + heat \rightarrow Mg + I_2 \qquad (33)$$

The elemental magnesium generated in reaction is then recycled to be used again for the treatment of a flue gas, as described above. The iodine generated in reaction (33) is sublimated and is recycled to reaction (24).

Figure 5:
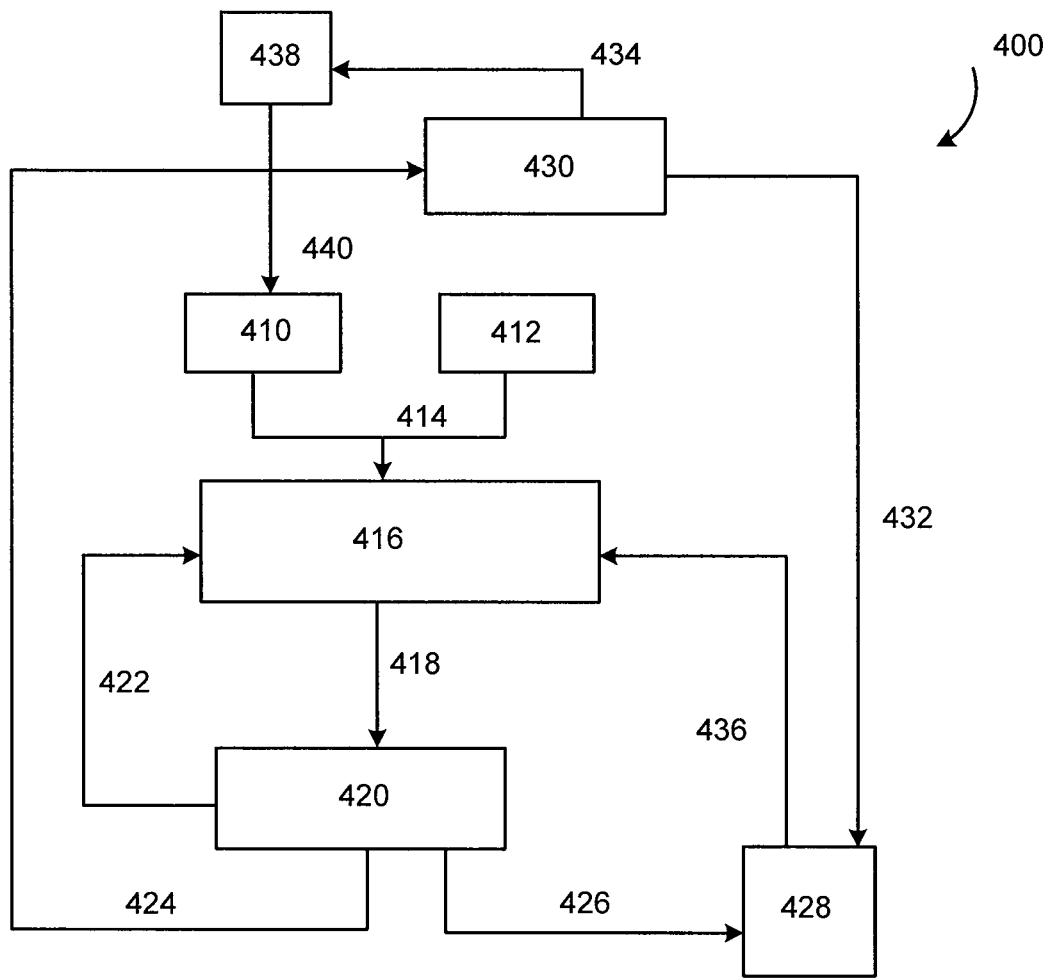
FIG. 5 is a schematic diagram of a process for the regeneration of elemental magnesium.

Referring now to FIG. 5, an exemplary process for the regeneration and recycling elemental magnesium is shown 400. Magnesium oxide which has been produced from treating a flue gas 410 as provided above, or optionally from a direct carbon fuel cell 412 as provided below, is optionally combined into a magnesium oxide stream 414. In, for example, a vessel 416, the magnesium oxide is reacted with hydrogen iodide, wherein the hydrogen iodide has been prepared as defined above. In particular, the hydrogen iodide is prepared by reacting iodine with water to produce hydrogen iodide and iodic acid. The reaction results in stream 418 containing magnesium iodide and magnesium iodate, stream 418 being heated in vessel 420 which generates magnesium oxide stream 422 which is returned to vessel 416 and magnesium iodide stream 424. The heating of stream 418 also results in an iodine and oxygen stream 426 which is separated in vessel 428. Magnesium iodide stream 424 is heated, optionally in a vessel 430, to generate an iodine stream 432 and an elemental magnesium stream 434. Iodine streams 426 and 432, after being separated and purified in 428 are combined to form iodine stream 436 which is then returned to vessel 416 to begin the regeneration process again. Elemental magnesium stream 434 is used again to treat a flue gas as described above, which generates another magnesium oxide stream 440 and begins the process again 410.

Figure 6:
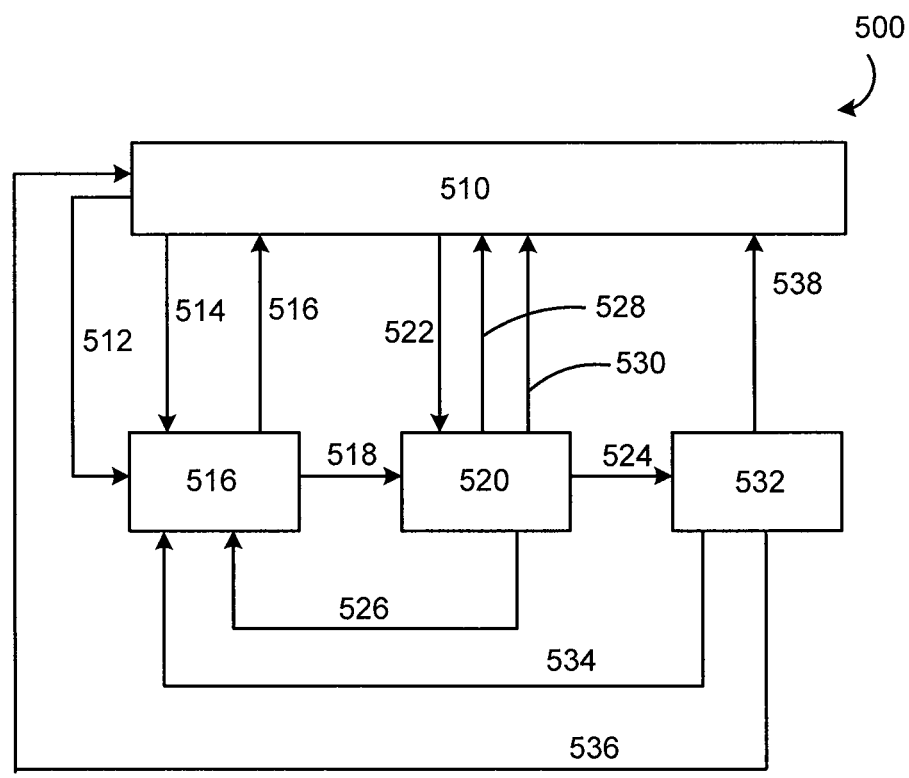
FIG. 6 is a schematic diagram of a heat recovery process for the regeneration of elemental magnesium.

Referring now to FIG. 6, an exemplary diagram demonstrating the inputs and outputs of thermal energy during the magnesium regeneration process is shown 500. The combustion of a carbon-based fuel, such as coal or natural gas, generates thermal energy and a flue gas, wherein the flue gas is treated in accordance with the disclosure in process 510. The combustion of the fuel and the treatment of the flue gas generates a magnesium oxide stream 512 and a hot water and/or steam stream 514, which provides the thermal energy for the reaction of iodine with hot water 516 to generate the hydrogen iodide and begin the regeneration reactions. The generation of hydrogen iodide in 516 is exothermic, which thermal energy stream 516 is returned to the process 510. The magnesium oxide and hydrogen iodide react at 520 which is an endothermic process and therefore requires energy 522 from the process 510, which generates elemental magnesium stream and iodine stream 524. Unreacted magnesium oxide stream 526 is returned to 516. The process 520 also generates oxygen stream 528 and steam stream 530 at a temperature of less than about 600° C. The magnesium and iodine stream 524 are cooled at 532 and separated into iodine stream which is returned to process 516 and elemental magnesium stream 536 which is regenerated and returned to further treat a flue gas in process 510. The cooling process 532 also releases thermal energy stream 538 which is returned to process 510.

(III) Direct Carbon Fuel Cell

As described above in reactions (1) and (2), when elemental magnesium is burned in a flue gas to remove carbon dioxide and carbon monoxide from the flue gas, magnesium oxide and molecular carbon are produced. Accordingly, in one embodiment of the present disclosure, there is also included a process for utilizing the molecular carbon in a direct carbon fuel cell.

Direct carbon fuel cells (DCFC) are well known to those skilled in the art, see for example U.S. Pat. No. 555,511 to Jacques or U.S. Pat. No. 7,910,258 to Steinberg. Direct carbon fuel cells generate electricity by converting a carbon-based fuel, such as coal, directly into electricity. When coal is used as the fuel in a DCFC, impurities in the coal must be removed before being utilized in the DCFC, which therefore increases the time and cost related to the DCFC process. Coal often results in the DCFC becoming clogged due to the impurities that are present in the coal. In addition, typical DCFCs release carbon dioxide into the atmosphere.

Accordingly, in one embodiment of the disclosure, the relatively pure molecular carbon generated in reactions (1) and (2), which includes purities of greater than 90%, or 95%, or 100%, is utilized in a DCFC to generate electricity. As shown in reaction (34), a DCFC produces electricity from the molecular carbon fuel, and also produces carbon dioxide as a waste product.

$$C+O_2+\text{heat} \rightarrow CO_2+\text{electricity} \quad (34).$$

Accordingly, in one embodiment, the molecular carbon generated in reactions (1) and (2) is utilized in a DCFC to generate electricity, and carbon dioxide, wherein the carbon dioxide is then recycled to reaction (1) resulting in a closed, continuous process. As a result, there is no emission to the atmosphere of $CO_2$. In another embodiment, the elemental carbon obtained from, for example, reactions (1) and (2), has a purity, for example, of at least about 90%, optionally about 95%, suitably about 99%, and accordingly, there is minimal (less than 10%, optionally less than about 5%, suitably less than about 1%) production in the DCFC process of other flue gases, such as nitrogen dioxide and/or sulfur dioxide. In another embodiment, additional cycles of the elemental carbon through the flue treatment process and the DCFC process, results in greater purity of the elemental carbon, resulting in purities of the elemental carbon of at least about 95%, suitably about 99%. Accordingly, in one embodiment, with additional carbon cycles, carbon dioxide and/or carbon monoxide comprises the major product from the DCFC process (greater than about 95%, suitably about 99%, or about 99.9%). In another embodiment, the carbon dioxide or carbon monoxide, being the major flue gases, or the only flue gases, from the DCFC process, are redirected to be burned again with elemental magnesium to complete the cyclical process. In one embodiment, the cyclical process increases the efficiency of the fuel burning process, and the production of thermal and electrical energy In one embodiment, the DCFC used in accordance with the present disclosure requires thermal energy to heat the fuel cell to temperatures between 600° C. and 800° C. In addition to the molecular carbon used in the DCFC process (and generated from reaction (1)), the DCFC process also utilizes oxygen to increase the efficiency of the DCFC process. In one embodiment, the treatment of a flue gas as described above, provides all of the necessary components for the DCFC process. In particular, the treatment of a flue gas generates thermal energy as the burning of the magnesium results in temperatures that exceed 1100° C., and accordingly, this thermal energy is captured to provide the energy necessary for the DCFC process. In addition, in one embodiment, as described in reaction (1), molecular carbon is produced in the treatment of a flue gas, which provides the necessary carbon based fuel for the DCFC in relatively pure form. In one embodiment, the molecular carbon produced in reaction (1) is treated to increase the purity of the fuel for the DCFC. In addition, in one embodiment, when coupled with the magnesium recovery process described above, the system also produces oxygen utilized in the DCFC process.

Figure 7:
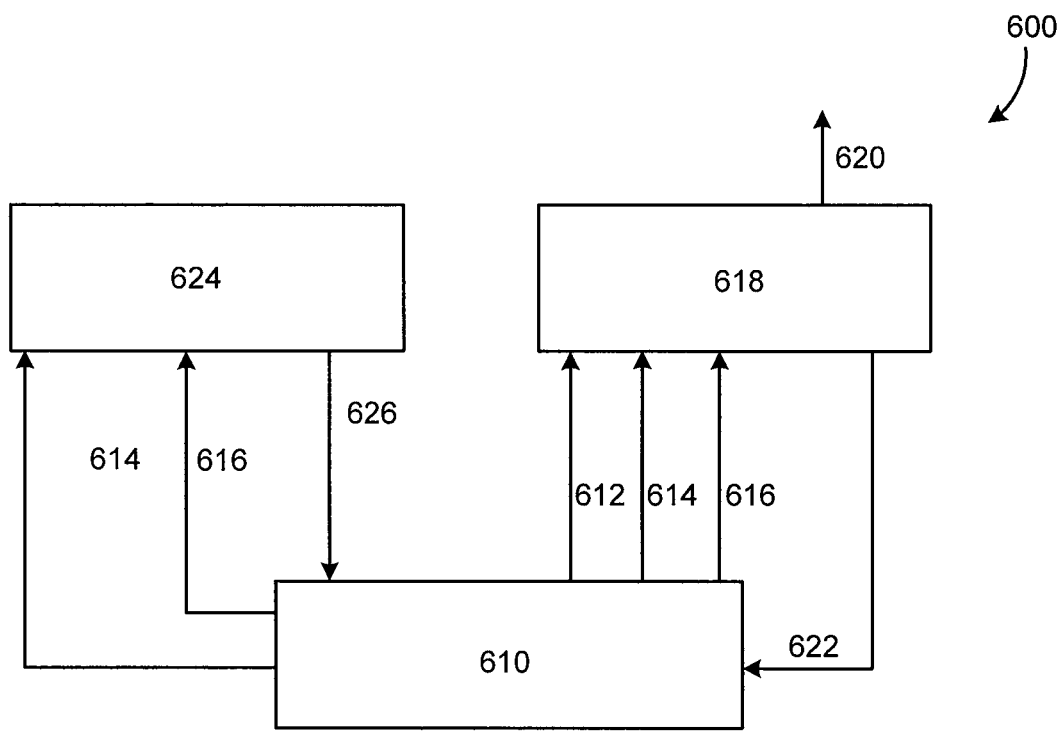
FIG. 7 is a schematic diagram of a process coupling a direct carbon fuel cell with a treatment of a flue gas.

Referring now to FIG. 7, an exemplary process 600 in which a direct carbon fuel cell is used in conjunction with the treatment of a flue gas is shown. The process of treatment of a flue gas as described above is shown at 610 and produces an elemental carbon stream 612 and a thermal energy stream 614. In addition, an oxygen stream 616 is also produced. These streams are preferably the required fuel for a direct carbon fuel cell process 618, which generates electrical energy 620, as well as a carbon dioxide stream 622. The carbon dioxide stream 622 also provides the fuel for the flue gas treatment process 610, completing the looped energy process. This process is also optionally used in combination with a thermoelectric power station 624 which combusts a carbon based fuel to generate a flue gas 626 which is used as an input in the process in 610. The thermal energy stream 614 and oxygen stream 616 may also be directed to the power station 624.

In one embodiment, the carbon dioxide produced in the DCFC is returned to a flue gas treatment process where it is again treated with elemental magnesium, and forming elemental carbon, which is subsequently treated again through the DCFC. Accordingly, a cycle of carbon is locked in the processes and is repeated several times, each time generating energy. In addition, no nitrogen and/or sulfur dioxides are produced in these processes.

Figure 8:
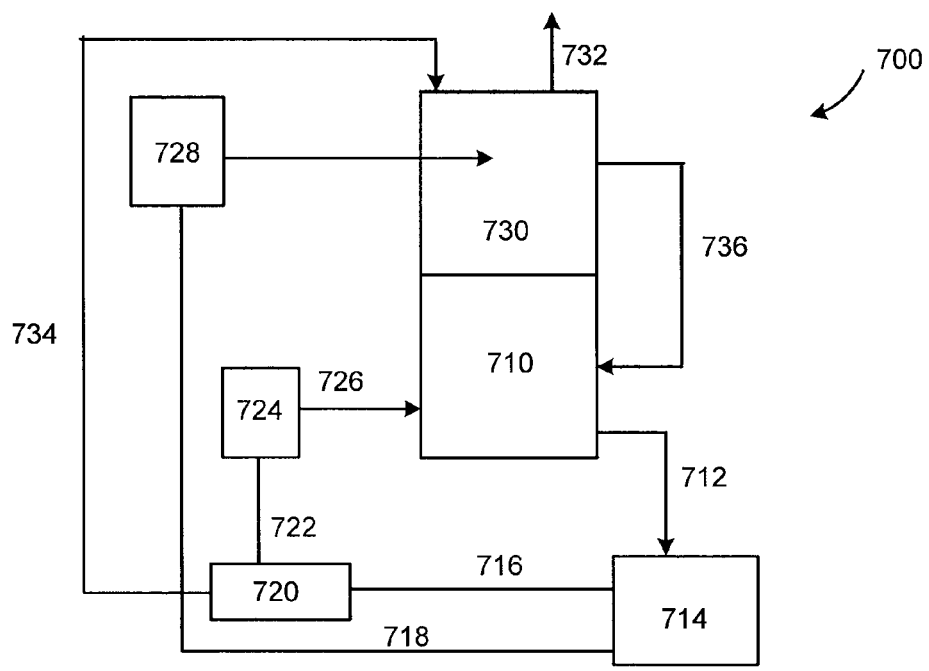
FIG. 8 is a schematic diagram of a carbon cycle using a direct carbon fuel cell.

Referring now to FIG. 8, an exemplary cyclical carbon process 700 for producing energy is shown. In combustion chamber 710, carbon dioxide (from a flue gas for example) is burned in the presence of elemental magnesium, which produces thermal energy, as well as different powders 712 including elemental carbon and magnesium oxide. The powders are separated 714, using for example centrifugation, to recover at least a magnesium oxide stream 716 and an elemental carbon stream 718. The magnesium oxide stream is treated using the process of the present disclosure to regenerate magnesium 720 and produce an elemental magnesium stream 722, which is transferred to a magnesium supply system 724, wherein the elemental magnesium enters the combustion chamber 710 through 726. Elemental carbon stream 718 is formed into a carbon rod 728 which is used in the direct carbon fuel cell 730 to produce electrical energy. In process 720, oxygen stream is also produced which is utilized in the direct carbon fuel cell 730. Carbon dioxide stream 736 is generated from the direct carbon fuel cell 730, is optionally compressed, and transferred to the combustion chamber 710 to be burned again in the presence of elemental magnesium, completing the carbon cycle. Accordingly, the cyclical process generates the production of energy without the use of thermal generating power plants.

Figure 9:
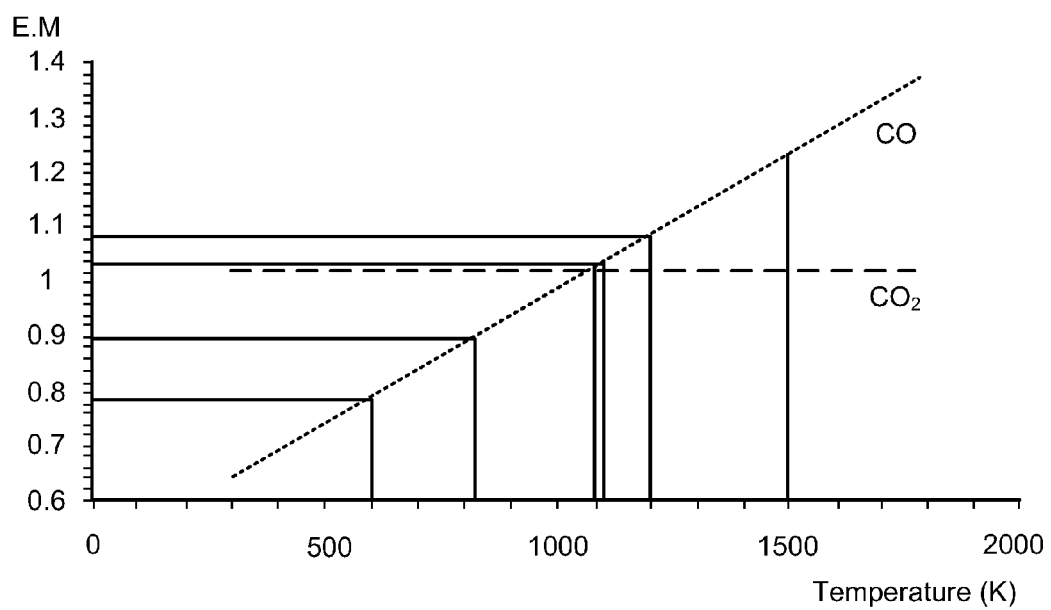
FIG. 9 is a graph showing the temperature relationship between carbon monoxide and carbon dioxide production in a direct carbon fuel cell.

In one embodiment, the temperature of the DCFC process is conducted between 1100° C. to 1200° C. which increases the efficiency of the DCFC process, and reduces the consumption of magnesium, by a factor of two. Accordingly, in one embodiment, the DCFC generates carbon monoxide rather than carbon dioxide, at higher temperatures, as shown in the graph in FIG. 9. Accordingly, when the carbon monoxide is returned to the combustion chamber, only one mole of magnesium is required per mole of carbon monoxide (Mg+CO→MgO+C), as opposed to two moles of magnesium when carbon dioxide is returned to the combustion chamber (2Mg+CO$_2$→2MgO+C). However, both processes return the same amount of elemental carbon to the DCFC.

(IV) Production of Methane

As described above, when the flue gas from a natural gas fired power plant is treated using the process of the present disclosure, the main products formed, as shown in reactions (17)-(20), are molecular carbon, hydrogen gas and magnesium oxide.

Accordingly, in one embodiment, the molecular carbon and hydrogen gas produced as products from the treatment of a natural gas flue gas are used to produce methane gas.

In one embodiment, the production of methane gas is generated by heating molecular carbon and hydrogen gas in the presence of a catalyst, such as powdered nickel, as shown in reaction 35:

$$C(s, graphite) + 2H_2(g) + \text{nickel catalyst} \rightarrow CH_4 + \text{heat} \quad (35)$$

In one embodiment, the reaction (35) is conducted at temperatures between 500° C. to 800° C., and reaction releases about 74.9 KJ/mol.

In one embodiment, the resulting methane from reaction (35) is burned in the natural gas fired power plant.

(V) Sabatier Reaction

As known to those skilled in the art, the Sabatier reaction is a process which involves the reaction of hydrogen gas with carbon dioxide at elevated temperatures in the presence of a catalyst to produce methane and water.

The Sabatier reactions are generally described as follows in reactions (36)-(38):

$$CO + 3H_2 + \text{Ni catalyst} \rightarrow CH_4 + H_2O \quad (36)$$

$$2CO + 4H_2 + \text{Fe catalyst} \rightarrow C_2H_4 + 2H_2O \quad (37)$$

$$CO_2 + 4H_2 + \text{Ni, Cu}_2\text{O catalyst} \rightarrow CH_4 + 2H_2O \quad (38)$$

As described above, when the flue gas from a natural gas fired power plant is treated using the process of the present disclosure, the main products formed, as shown in reactions (17)-(20), are molecular carbon, hydrogen gas and magnesium oxide. Accordingly, in one embodiment, the hydrogen gas produced is utilized in a Sabatier reaction to generate methane, or other low boiling hydrocarbons. As the hydrogen gas is generated as a side product of reactions (17)-(20), it is not necessary to use hydrogen gas prepared from typical sources, such as hydrocarbon sources.

In one embodiment, the molecular carbon generated in reactions (17)-(20) is utilized to generate CO or CO$_2$, which is then reacted in the Sabatier reactions to generate methane. Accordingly, in one embodiment, the molecular carbon is oxidized under appropriate conditions to form CO or CO$_2$ as shown in reactions (39) and (40).

$$C(s) + \tfrac{1}{2}O_2(g) \rightarrow CO(g) + \text{heat} \quad (39)$$

$$2CO(g) + O_2(g) + \text{catalyst} \rightarrow 2CO_2(g) + \text{heat} \quad (40)$$

$$C(s) + O_2 \rightarrow CO_2(g) + \text{heat} \quad (41)$$

The generation of carbon monoxide from molecular carbon as in reaction (39) is formed during oxidation of carbon under conditions where there is a lack of oxygen. This process is exothermic such that about 111.6 kJ/mol of heat is released during the reaction. As shown in reaction (40), carbon monoxide is oxidized in the presence of oxygen to carbon dioxide, and in the process releasing 566 kJ/mol of heat. Finally, as shown in reaction (41), molecular carbon is oxidized in the presence of oxygen by burning the carbon to form carbon dioxide, which releases 394.5 kJ/mol of heat.

Accordingly, all of the required components of the Sabatier reactions are formed, or are easily formed, from the products of the flue gas treatment process, when the flue gas originates from natural gas.

(VI) Processes

In one embodiment, it will be understood that the treatment of any flue gas by burning an amount of magnesium in the flue gas may be used without any of the above additional processes, or may be used in combination with some or all of the above processes.

Accordingly, for example, the treatment of a flue gas is used in combination with the process for regenerating elemental magnesium from magnesium oxide. In particular, the magnesium oxide that is produced in reactions (1) and (2), for example, is processed through the magnesium regeneration process to recover elemental magnesium, which is then recycled to the flue gas treatment process. In one embodiment, no additional electricity or thermal energy is required for the processes to proceed, and as such, the reactions proceed solely on the energy produced during each of the reactions.

In another embodiment, the treatment of any flue gas is used in combination with both the process for the regeneration of elemental magnesium and the direct carbon fuel cell. Accordingly, in one embodiment, in addition to the magnesium oxide that is produced in reactions (1) and (2) being treated to regenerate the elemental magnesium, the molecular carbon from reactions (1) and (2) is treated in a DCFC to produce electrical energy. In one embodiment, as the DCFC process generates carbon dioxide, the carbon dioxide can be recovered and burned again in elemental magnesium.

In another embodiment, the treatment of any flue gas, such as the flue gas from a natural gas, is used in combination with both the process for the regeneration of elemental magnesium and the Sabatier reactions or the production of methane. Accordingly, in one embodiment, in addition to the magnesium oxide that is produced in reactions (1) and (2) being treated to regenerate the elemental magnesium, the molecular carbon from reactions (1) and (2) is reacted with hydrogen gas to form methane, which can be burned again. Alternatively, the molecular carbon is reacted with oxygen to form carbon dioxide which is subsequently reacted with the hydrogen gas to generate methane, which can also be burned again.

It will also be understood that in one embodiment, the processes of the present disclosure are performed separately. Accordingly, for example, the molecular carbon generated from reactions (1) and (2) is transported to another site to be used in a DCFC or to be used in a Sabatier reaction.

EXAMPLES

Example 1

Energy Calculations for Magnesium (Mg) Recovery

One kilogram of coal emits 2.931 kg of carbon dioxide, which therefore requires 3.237 kilograms of magnesium to be burned for the treatment of the flue gas. Accordingly, upon treating the flue gas, 5.367 kg of magnesium oxide are produced, from 1 kg of coal.

Based on the recovery of 5.367 kg of magnesium oxide, the total energy absorbed by the magnesium recovery processes is 7.057 MJ.

During the preparatory phase of the magnesium recovery processes, specifically, the generation of hydrogen iodide (see reaction (20)), is an exothermic reaction, which releases about 30 MJ of heat energy. During the first regeneration stage in which hydrogen iodide is mixed with magnesium oxide (see reaction (21)), this reaction is endothermic and requires approximately 7.753 MJ of energy.

As the temperature of the mixture is increased such that the magnesium hydroxide and iodate are decomposed, and finally the magnesium iodide decomposes to elemental magnesium (see reactions 25-27), these reactions require about 29.32 MJ. Accordingly, the entire reaction system to recover and recycle elemental magnesium from magnesium oxide using hydrogen iodide requires about 7.057 MJ of thermal energy.

However, the processes of the disclosure produce excess thermal energy such that no external energy is required for the recovery of elemental magnesium. In particular, thermoelectric power stations which burn coal release excess heat energy which can be captured for the reactions 24-27. In addition, heat energy is released when the flue gas is treated by burning elemental magnesium in the flue stream. Finally, heat energy is also produced when elemental magnesium is combusted in the flue gas due to the presence of oxygen.

In particular, the combustion of 1 kg of coal in a thermoelectric power plant releases between 22-24 MJ, while the combustion of magnesium with 2.931 kg of carbon dioxide releases about 13.945 MK of energy. In addition, the combustion of magnesium with 2.999 kg of oxygen releases 85.49 MJ. Accordingly, the total energy released from such reactions is approximately 122.436 MJ (all reactions are standardized to the combustion of 1 kg of coal).

The combustion of one kilogram of coal produces 2.931 kg of carbon dioxide. Such amount of carbon dioxide requires 3.237 kg of magnesium to combust with the $CO_2$ to form magnesium oxide (5.368 kg) and carbon (0.8 kg). In addition, the combustion of such an amount of coal also generates 2.999 kg of oxygen, which also reacts with elemental magnesium, and requires 4.556 kg of magnesium to combust. Accordingly, the total consumption of magnesium for the combustion of 1 kg of coal is 7.793 kg. Accordingly, to regenerate such an amount of magnesium (oxide), the process requires an input of 16.99 MJ of thermal energy for every one kilogram of coal combusted.

The magnesium oxide that is reacted as in reaction (21) does not proceed with 100% efficiency. The reaction proceeds with about 83% efficiency, and therefore, the remaining 17% is recycled to the reaction, which requires an additional 2.88 MJ of energy to regenerate. Accordingly, the total thermal energy which is required for the regeneration of magnesium oxide produced from burning elemental magnesium in the flue gas from one kilogram of coal is 19.879 MJ.

Accordingly, as approximately 122 MJ of energy is produced from burning one kilogram of coal in the processes of the disclosure, no electrical energy is required to regenerate and recycle the magnesium oxide that is produced from burning elemental magnesium (requiring 19.879 MJ of thermal energy), which is only 16.236% of the total energy of the system. A thermoelectric power system generally loses about 84.184 MJ (per kg of coal) to waste thermal energy, which is 68.722% of the total energy of the system. The process of the present disclosure to regenerate elemental magnesium requires only 16.236% of such energy, and accordingly, there is 52.486 of this waste thermal energy which is useful for any of the processes as described above where energy is required. As such, the process of regenerating the elemental magnesium from magnesium oxide requires only waste thermal energy generated in normal thermoelectric power stations. In addition, the magnesium and iodine, for example, produced in reaction (27), must be cooled down to be reused, which therefore releases heat which can also be recycled in the regeneration process.

The invention claimed is:

1. A process for treating a flue gas comprising:
   a) burning an amount of elemental magnesium in the flue gas.

2. The process of claim 1 wherein the flue gas comprises carbon dioxide, sulfur dioxide, carbon monoxide, and nitrogen dioxide.

3. The process of claim 2, further comprising igniting the amount of elemental magnesium.

4. The process of claim 2, wherein during the burning step, at least a first portion of the amount of elemental magnesium reacts with at least a portion of the carbon dioxide to yield magnesium oxide, carbon, and ultraviolet light.

5. The process of claim 2, wherein during the burning step, at least a second portion of the amount of elemental magnesium reacts with at least a portion of the carbon monoxide to yield magnesium oxide, carbon, and ultraviolet light.

6. The process of claim 1, wherein during the burning step, at least a third portion of the amount of elemental magnesium reacts with at least a portion of the sulfur dioxide to yield magnesium oxide, ultraviolet light, and at least one of elemental sulfur and magnesium sulfide.

7. The process of claim 4, whereby (i) at least a first portion of the nitrogen dioxide is exposed to the ultraviolet light and is decomposed into nitric oxide and monatomic oxygen; (ii) at least a second portion of the nitrogen dioxide is exposed to the ultraviolet light and is decomposed into monatomic nitrogen and monatomic oxygen (iii) at least a portion of the nitric oxide is exposed to the ultraviolet light and is decomposed into monatomic nitrogen and monatomic oxygen; (iv) and at least a first portion of the monatomic oxygen reacts with a fourth portion of the amount of elemental magnesium to produce magnesium oxide; and (v) at least a first portion of the monatomic nitrogen reacts with a fifth portion of the amount of elemental magnesium to produce magnesium nitride.

8. The process of claim 4, further comprising exposing a solar cell to at least a portion of the ultraviolet light to generate electricity from the solar cell.

9. The process of claim 1, wherein the flue gas further comprises water vapor, and wherein at least a portion of the water vapor reacts with at least a sixth portion of the amount of elemental magnesium to yield magnesium oxide and hydrogen gas.

10. The process of claim 1, further comprising:
   (i) passing the amount of elemental magnesium into a conduit,
   (ii) passing the flue gas into the conduit, and
   (iii) igniting and burning the amount of elemental magnesium in the conduit to yield a mixture of heated gases and powders.

11. The process of claim 10, further comprising transporting the mixture to a heat transfer chamber wherein heat from the mixture is used to generate energy.

12. The process of claim 10, further comprising separating the gases from the powders.

13. The process of claim 1, wherein the amount of elemental magnesium is in the form of a powder, rod, brick or any combination thereof.

14. The process of claim 10, wherein the flue gas further comprises oxygen, and prior to step (iii), the process further comprises pre-treating the flue gas to remove the oxygen.

15. The process of claim 14, wherein pretreating the flue gas comprises exposing the flue gas to silane, whereby the silane reacts with the oxygen to yield silicon dioxide and water.

16. The process of claim 14, further comprising exposing the flue gas to amorphous silicon, whereby the amorphous silicon reacts with monatomic nitrogen in the flue gas to yield silicon nitride.

17. The process according to claim 1, further comprising obtaining at least a magnesium oxide (MgO) fraction and a molecular carbon (C) fraction from the burning step.

18. The process according to claim 17, wherein after the burning step, the magnesium oxide fraction is further reacted with hydrogen iodide (HI) to obtain a magnesium iodide ($MgI_2$) fraction.

19. The process according to claim 18, wherein the hydrogen iodide is obtained by contacting iodine ($I_2$) with water.

20. The process according to claim 18, wherein the magnesium iodide fraction is heated to a temperature suitable to obtain an elemental magnesium fraction and an iodine ($I_2$) fraction.

21. The process according to claim 19, wherein the temperature suitable to obtain the elemental magnesium fraction is between about 600° C. and 800° C.

22. The process according to claim 20, wherein the elemental magnesium fraction is recycled to the burning step in claim 1.

23. The process according to claim 20, wherein the iodine fraction is recycled and contacted with water to obtain the hydrogen iodide.

24. The process according to claim 17, wherein the molecular carbon fraction is utilized in a direct carbon fuel cell to generate electrical energy and a carbon dioxide ($CO_2$) fraction.

25. The process according to claim 24, wherein the carbon dioxide fraction is recycled to the burning step in claim 1.

26. The process according to claim 1, wherein the flue gas is generated from combustion of natural gas, and the process further comprises obtaining at least a magnesium oxide (MgO) fraction, a molecular carbon (C) fraction and a hydrogen ($H_2$) gas fraction.

27. The process according to claim 26, wherein the molecular carbon fraction is reacted with hydrogen gas in the presence of a suitable catalyst to obtain a methane gas fraction.

28. The process according to claim 27, wherein the suitable catalyst comprises powdered nickel.

29. The process according to claim 26, wherein the molecular carbon fraction is oxidized to obtain a carbon dioxide fraction.

30. The process according to claim 29, wherein the carbon dioxide fraction and the hydrogen gas fraction are reacted in the presence of a suitable catalyst to obtain a methane gas fraction.

31. The process according to claim 30, wherein the methane gas fraction is combusted to obtain thermal energy and a natural gas flue gas.

32. The process according to claim 31 wherein the natural gas flue gas is recycled back into the burning step.

* * * * *